United States Patent
Casuse et al.

(10) Patent No.: US 12,365,998 B2
(45) Date of Patent: Jul. 22, 2025

(54) ION EXCHANGE MEMBRANE SEPARATED TWO ELECTRODE FLOW ANALYZER FOR CONTINUOUS AQUEOUS ELECTROCHEMICAL HEAVY METAL DETECTION

(71) Applicant: UNM RAINFOREST INNOVATIONS, Albuquerque, NM (US)

(72) Inventors: Tybur Quinton Casuse, Albuquerque, NM (US); Fernando Garzon, Santa Fe, NM (US); Jose Manuel Cerrato Corrales, Albuquerque, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 156 days.

(21) Appl. No.: 17/356,203

(22) Filed: Jun. 23, 2021

(65) Prior Publication Data

US 2021/0395910 A1 Dec. 23, 2021

Related U.S. Application Data

(60) Provisional application No. 63/042,921, filed on Jun. 23, 2020.

(51) Int. Cl.
*C25B 11/081* (2021.01)
*C25B 9/23* (2021.01)
(Continued)

(52) U.S. Cl.
CPC .............. *C25B 11/081* (2021.01); *C25B 9/23* (2021.01); *C25B 11/032* (2021.01);
(Continued)

(58) Field of Classification Search
CPC .. G01N 33/1813; G01N 27/304; G01N 27/31; H01M 4/8867
See application file for complete search history.

(56) References Cited

U.S. PATENT DOCUMENTS 3,966,579 A * 6/1976 Chang ................ G01N 27/4045
429/432
4,025,412 A * 5/1977 LaConti ............. G01N 27/4045
204/426
(Continued)

OTHER PUBLICATIONS

Cao et al, "Nafion membranes as electrolyte and separator for sodium-ion battery", International Journal of Hydrogen Energy, Jan. 23, 2014, 39, 16110-16115. (Year: 2014).*

(Continued)

*Primary Examiner* — Luan V Van
*Assistant Examiner* — Andrew Koltonow
(74) *Attorney, Agent, or Firm* — MH2 Technology Law Group LLP

(57) ABSTRACT

An ion exchange membrane separated two electrode flow analyzer for continuous aqueous electrochemical heavy metal detection is disclosed. The electrochemical cell includes a gas diffusion counter/reference electrode, a flooded flow through working electrode, and an ion exchange membrane that separates the gas diffusion counter/reference electrode and the flooded flow through working electrode. A method of continuous fluid analysis using a multi-electrode flow analyzer is also disclosed, including passing an aqueous sample through a first inlet flow area and into a working electrode of a multi-electrode flow analyzer, passing a gas mixture through a second inlet flow area and into a counter/reference electrode of the multi-electrode flow analyzer, depositing an analyte onto a surface of the working electrode, stripping the analyte from the surface of the
(Continued)

working electrode by sweeping a range of a potential applied to the surface of the working electrode.

21 Claims, 4 Drawing Sheets

(51) Int. Cl.
  *C25B 11/032* (2021.01)
  *C25B 11/065* (2021.01)
  *C25B 13/00* (2006.01)
  *G01N 27/30* (2006.01)
  *G01N 27/333* (2006.01)
(52) U.S. Cl.
  CPC ............ *C25B 11/065* (2021.01); *C25B 13/00* (2013.01); *G01N 27/304* (2013.01); *G01N 27/333* (2013.01)

(56) References Cited

U.S. PATENT DOCUMENTS

| | | | | |
|---|---|---|---|---|
| 5,997,706 | A * | 12/1999 | Kiesele | G01N 27/4045 204/415 |
| 6,682,647 | B1 * | 1/2004 | Wang | G01N 27/42 205/789.5 |
| 9,134,267 | B2 * | 9/2015 | Clochard | G01N 27/423 |
| 2003/0049509 | A1 * | 3/2003 | Divisek | H01M 8/1009 429/410 |
| 2004/0197630 | A1 * | 10/2004 | Wilson | H01M 8/248 429/465 |
| 2004/0224214 | A1 * | 11/2004 | Vamos | H01M 8/1053 429/534 |
| 2006/0040163 | A1 * | 2/2006 | Yang-Tse | H01M 8/04156 429/535 |
| 2008/0245670 | A1 * | 10/2008 | Compton | G01N 27/48 204/290.1 |
| 2008/0278096 | A1 * | 11/2008 | Berjansky | H05B 41/36 315/291 |
| 2010/0021785 | A1 * | 1/2010 | Son | H01M 4/926 429/481 |
| 2011/0284395 | A1 * | 11/2011 | Dimitrakopoulos | G01N 27/42 204/406 |
| 2021/0131989 | A1 * | 5/2021 | Klein | G01N 33/54326 |

OTHER PUBLICATIONS

Kunimatsu et al, "Microtubular Hydrogen Electrode, a Reference Electrode for Electrochemical Analyses", Mar. 30, 2005, Journal of the Electrochemical Society, 152 (5), E161-E166. (Year: 2005).*

Muddemann et al, "Avoidance of Chlorine Formation during Electrolysis at Boron-Doped Diamond Anodes in Highly Sodium Chloride Containing and Organic-Polluted Wastewater", Oct. 30, 2018, Journal of the Electrochemical Society, 165 (15) J3281-J3287. (Year: 2018).*

\* cited by examiner

ION EXCHANGE MEMBRANE SEPARATED TWO ELECTRODE FLOW ANALYZER FOR CONTINUOUS AQUEOUS ELECTROCHEMICAL HEAVY METAL DETECTION

STATEMENT OF GOVERNMENT INTEREST

This invention was made with government support under 1914490, and DGE1418062 awarded by the National Science Foundation. The government has certain rights in the invention.

TECHNICAL FIELD

The present teachings relate generally to an ion exchange membrane separated two electrode flow analyzer, and, more particularly, to an ion exchange membrane separated two electrode flow analyzer for use in continuous electrochemical analysis of heavy metals in an aqueous environment.

BACKGROUND

Continuous sampling, monitoring, and analysis of heavy metals and other analytes to evaluate water quality in aquifers during well drilling and other ground water monitoring applications would be advantageous to insure improved environmental monitoring, accurate industrial wastewater remediation protocols, and reduced costs in water treatment. In particular, there is a current need for an inline arsenic sensing system that can continuously sample and ground water monitoring applications. Concentrations of arsenic oxyanions above 10 µg/L in drinking water are considered dangerous by the World Health Organization. Levels above 10 µg/L in drinking water in daily consumption can lead to renal toxicity and a condition known as arsenicosis, which produces lesions on the skin.

Conventional means of heavy metal and other analyses utilize a batch determination or analysis as opposed to continuous sampling, monitoring, and analysis. Batch determination of analytes in ground water samples do not account for differences in analyte concentrations based on variations in seasonal or climate fluctuations, geographical variations, or changes in heavy metal contaminants over time. Water may penetrate geological features differently depending on the aforementioned factors or depth of penetration of sampling may yield different results or take too long for analysis results from batch determination to make timely judgment based on the results.

Continuous sampling, monitoring, and analysis of heavy metals and other analytes of interest provides several advantages. Monitoring of ground water, aquifers, or other sources potentially contaminated with arsenic and other harmful contaminants may be accomplished in real time, or in concert with other remediation operations. In an example where groundwater contamination results are desirable while drilling a well, continuous analysis allows for timely decisions related to well location and depth to be determined during drilling operations. In water quality analysis applications where remediation processes are dependent upon contaminant concentrations, continuous analysis may enable more accurate and cost-effective remediation processes to counteract said contaminants.

Therefore, it is desirable to have an electrochemical cell for analysis of heavy metals or other analytes of interest having ion selectivity and diffusivity, as well as pH of analysis for continuous determination of a water source, as opposed to batch determination.

SUMMARY

The following presents a simplified summary in order to provide a basic understanding of some aspects of one or more embodiments of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

An electrochemical cell is disclosed. The electrochemical cell includes a gas diffusion counter/reference electrode, a flooded flow through working electrode, and an ion exchange membrane that separates the gas diffusion counter/reference electrode and the flooded flow through working electrode. The working electrode may include a physically vapor deposited gold (Au) film. The electrochemical cell may include a counter/reference electrode having a platinum (Pt) electrode. The working electrode may also include a hydrophilic surface. The working electrode may also include a porous carbon media. The working electrode may further include an internal serpentine fluidic pathway. The ion exchange membrane may include a cationic exchange membrane. The ion exchange membrane may include an anionic exchange membrane. The ion exchange membrane may include a near-neutral exchange membrane. The electrochemical cell may include a single stack fuel cell casing that encases the counter/reference electrode, the working electrode, and the ion exchange membrane. The electrochemical cell may include at least one inlet on a first side of the electrochemical cell, and at least one outlet on a second side of the electrochemical cell. The electrochemical cell may include a first inlet and a first outlet on a first side of the electrochemical cell, and a second inlet and a second outlet on a second side of the electrochemical cell.

An array of two or more electrochemical cells is also disclosed. The array of two or more electrochemical cells also includes a first electrochemical cell which may include a first gas diffusion counter/reference electrode, a first flooded flow through working electrode which may include a porous, hydrophilic media coated with a physically vapor deposited gold (Au) surface, and a first ion exchange membrane that separates the first gas diffusion counter/reference electrode and the first flooded flow through working electrode. The array of two or more electrochemical cells also includes a second electrochemical cell which may include a second gas diffusion counter/reference electrode, a second flooded flow through working electrode may include a porous, hydrophilic media coated with a bismuth surface, and a second ion exchange membrane that separates the second gas diffusion counter/reference electrode and the second flooded flow through working electrode.

The array of two or more electrochemical cells may include a single stack fuel cell casing that encases the first electrochemical cell and the second electrochemical cell. The first ion exchange membrane further may include an anionic exchange membrane. The second ion exchange membrane further may include a cationic exchange membrane. The first electrochemical cell and the second electrochemical cell may be configured in series.

Also disclosed is a method of continuous fluid analysis using a multi-electrode flow analyzer. The method of continuous fluid analysis also includes passing an aqueous sample through a first inlet flow area and into a working electrode of a multi-electrode flow analyzer, passing a gas mixture through a second inlet flow area and into a counter/reference electrode of the multi-electrode flow analyzer, depositing an analyte onto a surface of the working electrode, stripping the analyte from the surface of the working electrode by sweeping a range of a potential applied to the surface of the working electrode. The method of continuous fluid analysis also may include determining a peak current over the range of the potential to determine a quantity of analyte deposited on the working electrode. The method of continuous fluid analysis using a multi-electrode flow analyzer may include reducing any aqueous metal ions present on the surface of the working electrode prior to stripping the analyte from the surface of the working electrode. The method of continuous fluid analysis using a multi-electrode flow analyzer may include oxidizing any aqueous metal ions present on the surface of the working electrode prior to stripping the analyte from the surface of the working electrode. Depositing an analyte onto a surface of the working electrode further may include holding the working electrode at a negative potential. Sweeping a range of a potential on the surface of the working electrode may be conducted from a positive value to a negative value.

BRIEF DESCRIPTION OF THE DRAWINGS

The accompanying drawings, which are incorporated in and constitute a part of this specification, illustrate embodiments of the present teachings and together with the description, serve to explain the principles of the disclosure. In the figures.

Figure 1:
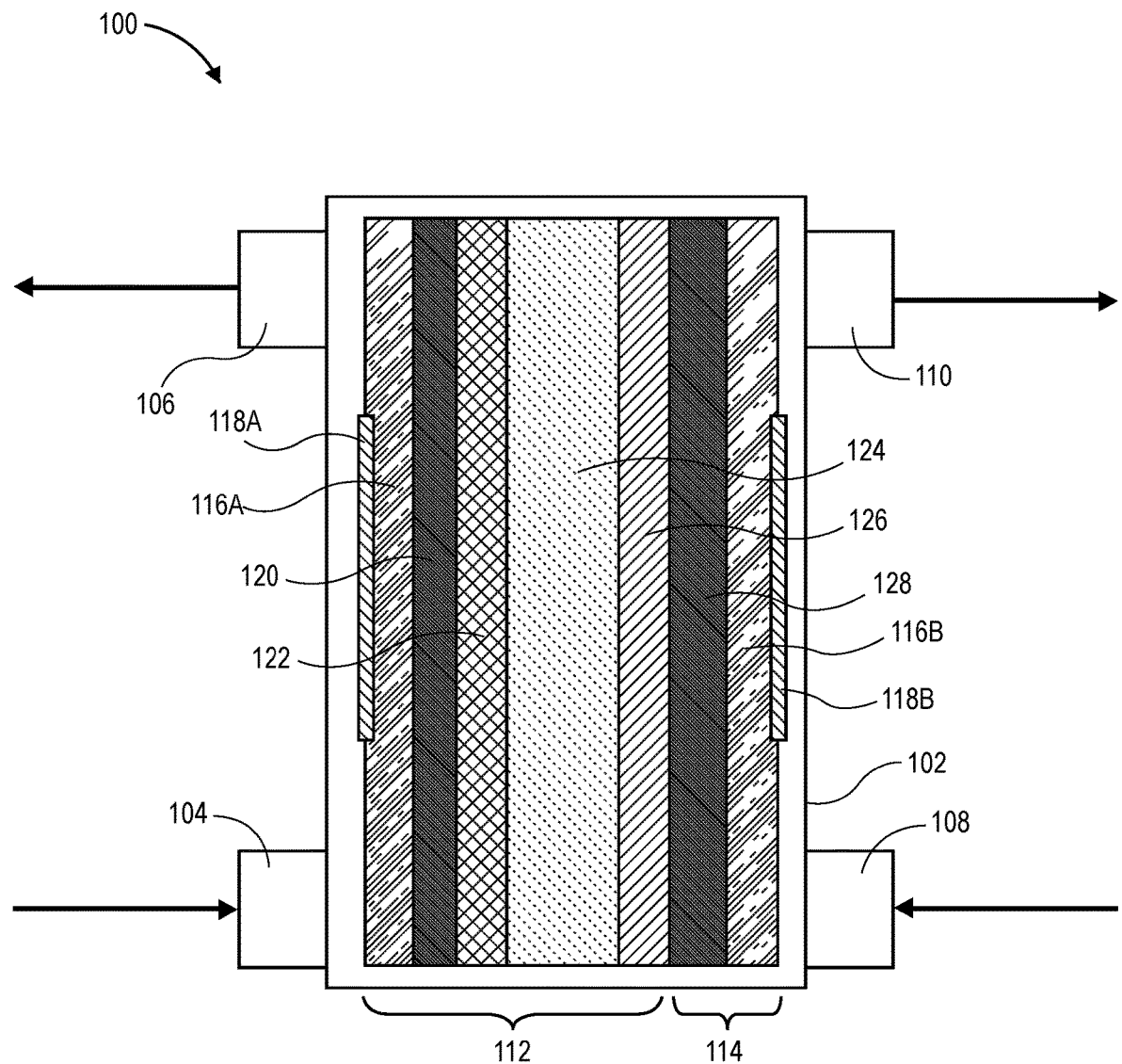
FIG. 1 is a cross-sectional schematic of a flow analyzer, according to an embodiment.

It should be noted that some details of the figures have been simplified and are drawn to facilitate understanding of the present teachings rather than to maintain strict structural accuracy, detail, and scale.

DETAILED DESCRIPTION

Reference will now be made in detail to exemplary embodiments of the present teachings, examples of which are illustrated in the accompanying drawings. Wherever possible, the same reference numbers will be used throughout the drawings to refer to the same, similar, or like parts.

There is a current need for a continuous, inline heavy metal sensing system that can continuously sample aquifer water quality for well drilling and ground water monitoring applications. One particular example of interest is the heavy metal arsenic. Concentrations of arsenic oxyanions above 10 µg/L in drinking water are considered dangerous by the World Health Organization. Levels above this in daily consumption may lead to renal toxicity and a condition known as arsenicosis, which produces lesions on the skin. Disclosed herein is a continuous fluid flow analyzer including a gold-based thin film, arsenic stripping voltammetry flow cell to meet this need.

Also disclosed herein is an electrochemical cell used in the analysis of heavy metals in water comprised of an ion exchange membrane (IEM) acting as separator and electrolyte, a combined reference and counter gas diffusion electrode, and a continuous flow flooded working electrode. The use of an ion exchange polymer electrolyte instead of the typical liquid electrolyte for stripping voltammetry allows for analysis of an analyte stream without having to extract samples from the stream and injecting them into a separate electrochemical cell containing a liquid electrolyte of the desired pH. This use of an IEM also allows for control of ion selectivity and diffusivity, as well as for control of the pH of analysis by selection of a polymer electrolyte having the appropriate pH to perform a desired electroanalysis. This enhanced control of analysis conditions enables the measurement and analysis of a wide range of possible metal analytes. In an embodiment, the separation of the counter electrode and working electrode in an electrochemical stripping analysis significantly decreases the unintentional oxidation of the analyte by the counter electrode compared to a traditional three electrode cell. The configuration of the IEM within the flow analyzer also reduces the need to increase the ionic conductivity, for example, acidification or buffering, of the sample prior to analysis. By flowing or introducing a known quantity of hydrogen gas over a platinum containing counter electrode, the hydrophobic gas diffusion counter/reference electrode acts as a stable potential reference electrode, thus eliminating the need for a third reference electrode in the cell. The flooded hydrophilic working electrode allows for continuous determination of a target species within a water source, as opposed to batch determination. This enhanced control of analysis conditions by use of the IEM, the elimination of a third reference electrode, and the continuous determination capabilities of this cell have substantial implications for applications of aqueous heavy metals analysis.

In certain embodiments described herein, an electrochemical cell with three primary components is disclosed. The electrochemical cell includes an ion exchange membrane acting as separator and electrolyte, a gas diffusion counter/reference electrode (CRE), and a flooded flow through working electrode. The two-phase flow analysis electrochemical cell increases selectivity and sensitivity in the electrochemical detection of trace heavy metals in water. The electrochemical cell may utilize a physically vapor deposited Au film working electrode (WE), a platinum (Pt) on carbon combined counter/reference electrode (CRE) and a Nafion ion exchange membrane (IEM) separating them in certain embodiments. Advantages of this and other embodiments as disclosed herein include the ability to regenerate the acid ion exchange membrane by producing protons at the counter electrode via the oxidation of hydrogen gas thus regenerating the membrane, by the reaction of $H_2 = 2H^+ + 2e^-$ or similar. Other advantages include the ability to regenerate an alkaline ion exchange membrane via producing hydroxide ions at the counter electrode via the reduction oxygen gas according to reaction such as $\frac{1}{2} O_2 + H_2O + 2e^- = 2OH^-$. In addition, such continuous flow analyzers provide the ability to combine multiple cells to target different species and the ability to use a separate, yet coupled water electrolyzation device to produce or refresh or replenish the needed reference gases, for example, hydrogen gas for use with acid membranes and oxygen gas for use with alkaline membranes. FIG. 1 is a cross-sectional schematic of a flow analyzer, according to an embodiment. FIG. 1 illustrates a flow analyzer 100 which includes a cell casing enclosure 102. The cell casing enclosure 102 defines a water inlet 104 and a water outlet 106 on one side of the cell casing enclosure 102 of the flow analyzer 100. In other embodiments, the water inlet 104 and the water outlet 106 may be located on opposite sides of the cell casing enclosure 102 or in different orientations. The water inlet 104 and water outlet 106 may also be otherwise attached to one or more fluidic devices, such as pumps or other devices to actively or passively transfer fluid into and out from the flow analyzer 100 via the water inlet 104 and the water outlet 106, respectively. The cell casing enclosure 102 of the flow analyzer 100 also defines a gas inlet 108 and a gas outlet 110 on an opposite side of the water inlet 104 and the water outlet 106. Other embodiments may have the gas inlet 108 and gas outlet 110 in different orientations or in different locations on the cell casing enclosure 102. The gas inlet 108 and gas outlet 110 may be attached to a variety of gas sources or gas effluent pathways, respectively, depending upon the specific operating parameters and configurations of the other components of the flow analyzer 100. Within the flow analyzer 100 is indicated a flooded zone, where an aqueous sample is introduced into the flow analyzer 100 and in contact with the contents therein, and a gas zone 114, where a gas flowing into the flow analyzer 100 is introduced into and in contact with the contents therein. An electrode lead material 116A, 116B having an etched serpentine flow path, or internal serpentine fluidic pathway is located on the working electrode side and the counter/reference side of the flow analyzer 100, respectively, within each of the flooded zone 112 and the gas zone 114. A serpentine pathway is utilized to optimize fluid contact with the metal electrode and/or electrolyte interface. The electrode lead material 116A on the flooded zone 112 side of the flow analyzer 100 is in contact with a metal plate 118A which can be configured to contact and be electrically connected to a potentiostat, not shown here, but located externally to the flow analyzer 100. Certain embodiments of current collector or flow fields or electrode materials may have serpentine paths that may not be etched and may have serpentine paths within the electrode lead material created by other means known to one skilled in the arts, such as machining, molding, etching or 3D printing into the current collector/flow fields. The electrode lead material 116 is in contact with and adjacent to a thin film 120 layer that is composed of hydrophilic, conductive carbon felt, but may also be composed of other materials having a hydrophilic surface. Electrode lead materials may include electronic conducting materials that do not corrode in contact with the analyte solution. These may typically be made of carbon, such as graphite or carbon/polymer composites, however titanium, stainless steels, and other corrosion resistant metals could be used. Adjacent to the thin film 120 is a thin film electrode 122, which in combination with the electrode lead material 116A, carbon felt thin film 120, and metal plate 118A constitute the working electrode side in the flow analyzer 100. The thin film working or analysis electrode 122 may be composed of PVD gold, and in alternate embodiments, may be composed of materials such as bismuth (Bi), platinum (Pt), silver (Ag), palladium (Pd), iridium (Ir), rhodium (Rh), various forms of carbon such as graphite, glassy carbon, doped diamond films, and conductive oxides such as indium tin oxide, or combinations thereof. Adjacent to the thin film electrode 122 is an ion exchange membrane electrolyte 124, and adjacent to the ion exchange membrane electrolyte 124 is a layer made of platinum (Pt) particles deposited onto a carbon substrate 126. The Pt particles deposited on carbon 126, hydrophobic gas diffusion layer 128, electrode lead material 116B, and metal plate 118B constitute the counter/reference electrode side. The ion exchange membrane electrolyte 124 separates the gas diffusion counter/reference electrode and the flooded flow through working electrode. In between the layer of platinum particles deposited onto a carbon substrate 126 and the electrode lead material 116B in the gas zone 114 is a hydrophobic gas diffusion layer 128. The electrode lead material 116B on the gas zone 114 side of the flow analyzer 100 is in contact with a metal plate 118B which can be configured to contact and be electrically connected to a potentiostat, not shown here, but located externally to the flow analyzer 100.

While FIG. 1 presents a configured flow having same side inlet 104 and outlet 106 alternate embodiments of cell configurations may have a cross flow path. The general mechanical aspect of the flow analyzer 100 is illustrated as a single stack fuel cell casing enclosure 102. While not shown, as mentioned previously, a peristaltic pump may pass a water sample through the flow area or flooded zone 112 on the working electrode (WE) side of the ion exchange membrane electrolyte 124 (IEM). A gas flow controller, also not shown herein, passes a hydrogen gas mixture to the flow path or gas zone 114 above the counter/reference electrode (CRE) side of the ion exchange membrane electrolyte 124 (IEM). Stripping voltammetry techniques can be used for the reduction and oxidation of aqueous metal ions on the WE side of the cell. An external potentiostat connected to one or both of the metal plate 118 drives deposition of analytes at the WE surface by holding a negative potential for a determined amount of time. Subsequently, the potentiostat strips the reduced analyte from the surface of the WE by sweeping the potential on the WE from negative to positive. A peak in the current vs. potential curve from the stripping step can be directly correlated to the amount of analyte deposited. This described use of a flow through cell flow analyzer 100 allows for a continuous determination of a sample as opposed to batch analysis. This has implications for in-situ analysis of water systems which may have variation in metals concentrations over time, such as rivers, lakes, aquifers accessed by wells, and the like.

The use of the ion exchange membrane electrolyte 124 (IEM) separator in configurations as embodied herein increases sensitivity, selectivity, and ease of use. The sensitivity of detection is increased due to the ionomer decreasing the transport of charged ions to the electrode. This includes ions which may have been unintentionally oxidized after transporting to the CRE side of the IEM during the deposition step. In the deposition step, the CRE must be held at a positive potential to counter the negative potential of the WE. In a traditional 3-electrode cell the WE and the counter electrode (CE) are both submerged in the same solution. In this traditional arrangement, the CE may unintentionally cause the analyte to be oxidized by nascent oxygen generation or electrochemical means. This oxidation alters the concentration of the solutions of the analyte and therefore can affect accuracy. In the flow analyzer configurations as embodied herein, nascent oxygen crossover is limited by gas flow over the CRE and the IEM separation. Furthermore, electrochemical oxidation of the analyte does not occur because the CRE does not interact directly with the water sample during analysis.

Metal plates 118A, 118B may be selected from similar materials used as electrode lead materials 116A, 116B. These include electronic conducting materials that do not corrode in contact with the analyte solution. These may typically be made of carbon, such as graphite or carbon/polymer composites, however titanium, stainless steels, and other corrosion resistant metals could be used. The classes of ion exchange materials that can be used in exemplary embodiments as described herein are fairly large. Perfluorosulfonic acid polymers, Di-vinyl Benzene-Styrene sulfonic acid polymers, Polyethylene imide (PEI), Di-vinyl Benzene-Styrene quaternary amine polymers, may be used depending on the specifics of the target analyte and environmental conditions of analysis. Counter/reference electrode materials for alternate embodiments for such an analyzer that uses acid membranes may include electrodes that are known to oxidize hydrogen at high rates such as platinum, platinum alloys such as Pt—Ru, Pt—Ni, Pt—Cr, as well as palladium and palladium alloys. Counter/reference electrode materials for alternate embodiments for such an analyzer that uses alkaline membranes may include electrodes that are known to reduce oxygen in basic aqueous electrolytes at high rates such as platinum, nickel, silver, cobalt, Fe—N, and Co—N in carbon materials. In certain embodiments of flow analyzers, the hydrophobic gas diffusion layer media may be composed of carbon fiber hydrophobic polymer composite materials such as carbon-PTFE or other fluoropolymers, however carbon/silicone or other combinations of carbon and hydrophobic polymers may be used. The purpose of these materials is to allow gas permeation while blocking liquid diffusion out of the cell. Hydrophilic gas diffusion layer media may also be composed of carbon fiber felts or cloths sometimes treated to improve wetting.

In alternate embodiments, the ion exchange membrane composition can be chosen to enhance selectivity. For example, in an anionic exchange membrane (AEM) selectivity for negatively charged species is decreased, because anionic species will not be able to access the WE surface due to Donnan exclusion from the AEM. This would decrease the number of interfering anions with the analysis. Additionally, the transport of divalent and trivalent cations would be greatly inhibited in a proton exchange membrane such as Nafion. The diffusivity of the divalent and trivalent cations are orders of magnitude lower than that of protons in the membrane. For example, $H_3AsO_3$ would be able to enter the AEM.

However, in such an embodiment, the competing $Cu^{2+}$ ion would have greatly reduced potential to interact with the WE. The reduced diffusivity of the ions is due to exchange with the mobile ions of the IEM. For the case of Nafion the $H^+$ mobile ions would be exchanged for the $Cu^{2+}$ at the sulfonate end group. Over time concentration of $Cu^{2+}$ or other cations would occur and would change the conductivity and pH of the membrane. Use of a cation exchange membrane would have similar, but opposite selectivity effects. In this case the Nafion could be regenerated by holding a potential between the CRE and the WE which would oxidize H2 gas to $H^+$ ions and flood the membrane until the anions are once again exchanged for protons. This would reestablish the local pH conditions and improve conductivity of the membrane. The regeneration process, or degree of irreversible fowling, could be monitored by analyzing the DC current vs. time. A stable DC current over time would indicate the IEM is at its most protonated state. This regeneration process may have a limited number of cycles, and therefore, a comparison of the DC current after irreversible fowling occurred compared to initial current would indicate when replacement of the IEM is necessary.

In alternate embodiments, the pH of the analysis can be chosen by selecting a proton exchange membrane for low pHs, a hydroxide exchange membrane for high pHs or another cation (e.g. $Ca^+$, $K^+$) in place of protons for neutral pHs. The ability to control the pH of the electrolyte allows for analysis of many ions, because the pH conditions control the speciation of the metals. Additionally, the case of use is increased because acidification or buffering of the sample is not necessary. The IEM provides ionic conductivity between the WE and the CRE which allows for electrochemical control. In a traditional 3-electrode cell the sample would need to be acidified or buffered to create a circuit between the WE, CE, and reference electrode. This aspect, in particular, provides current embodiments with improved utility for in-situ determination of water samples. This case of configuration and enhanced selectivity also lends this type of flow analyzer to be used in an array, or combination, of flow analyzers for the purpose of continuous analysis of multiple analytes where the flow analyzers may be configured in series or in parallel.

Various configurations of the electrochemical cell may be present in alternate embodiments of a flow analyzer such as those described herein. Certain embodiments may have variations in the ionomer composition within the ion exchange membrane electrolyte. While the IEM is located between the WE and CRE in embodiments, the IEM may be composed of cationic or anionic membranes depending on the required pH needed for the target analyte. In embodiments where it may be favorable to work in basic conditions an anionic hydroxide mobile ion membrane would be selected for use in the flow analyzer. In embodiments where it may be favorable to work in acidic conditions, a cationic proton mobile ion membrane would be selected for use in the flow analyzer. In embodiments where it may be favorable to use a neutral pH, a neutral membrane such as a $Na^+$ or $K^+$ ion cationic membrane may be selected for use in the flow analyzer.

Certain embodiments of flow analyzers as described herein may employ a cationic IEM in the electrochemical cell. As an example analyte, the multivalent arsenic metalloid forms several oxyanions with As (III) and As (V) in inorganic forms. In an average sample of natural water with a pH between 6 and 9 the dominant ion would be $H_3AsO_3$, also known as arsenous acid. As arsenous acid is a neutral species it would be capable of entering the polymer electrolyte membrane in such an embodiment having a cationic IEM. However, an ion such as $Cu^{2+}$, which is a competing ion for similar voltammetric techniques, would not be able to diffuse to the WE as readily as the neutrally charged Arsenous acid. Therefore, selectivity for the $Cu^{2+}$ would be decreased and it would interfere with the analysis to a lesser extent. It should be expected that this exclusion would be applicable to other cations.

Certain embodiments of flow analyzers as described herein may employ a near neutral IEM in the electrochemical cell. As an example analyte, hexavalent chromium forms a monovalent acid oxyanion below pH=6.5. If the IEM were to be anionic but the mobile ion was to be exchanged with an ion besides OH so that the local pH is 6 the $HCrO_4^-$ could be reduced to $Cr_2O_3$ (s) and re-oxidized for detection. Because $HCrO_4^-$ is monovalent it would not be as strongly hindered by exchange with the mobile ions in the membrane.

Certain embodiments of flow analyzers as described herein may employ an anionic IEM in the electrochemical cell. As an example analyte, copper forms an aqueous neutrally charged ion, CuO, between pH 7.5 and 12.5 which could be reduced to Cuprite or Cu(s) between pH 10 and 12.5. This could be achieved using an anionic exchange membrane with hydroxyl mobile ions which would result in a high pH and could be used to perform stripping voltammetry in the pH region described above. A secondary IEM coated onto the WE in any of the previously described embodiments would also aid in controlling the speciation at the electrode surface, while the primary IEM separator could control the species potentially interacting with the CRE. It should d be further noted that any one or combination of the previously described embodiments having various IEM compositions as described may be used in any of the exemplary embodiments of a continuous flow analyzer as described herein.

Certain embodiments of a continuous flow analyzer may have modifications or alternate configurations of the flooded working electrode, such as the use of a hydrophilic substrate for the metal electrode film to influence a complete wetting of the electrode. Alternatively, the WE electrode may be coated with a second ion exchange membrane in order to further improve or control analyte selectivity. While in illustrated embodiments, the CRE is a Pt containing electrode a hydrophobic gas diffusion layer is also used to limit the amount of water crossover, which would then be sent into the gas effluent. The gas flowing over the CRE should contain a known amount of hydrogen to allow for hydrogen oxidation and proton reduction to occur at the Pt CRE surface. Other enhancements may improve performance or alternate embodiments of flow analyzers as described herein including maximizing the surface area on the reference electrode. Additionally, if the working electrode contains gold, lower loading in the microgram/cm2 range may be employed to reduce costs. While counter electrode materials commonly include platinized electrodes of thin film gold, the target analyte may dictate the electrode material.

It should be noted that additional elements to the flow analyzer system not completely described herein may be utilized in accessory to or in conjunction with any or all features or the exemplary embodiments of flow analyzers. For example, various methods known to those skilled in the art may be utilized in combination with flow analyzers described herein to monitor flow of incoming water or fluid for analysis in order to correlate, calibrate, and determine analyte concentration based on the voltammetry results. Additionally, other auxiliary devices may be necessary, such as hydrogen detectors to enable determination of the "life" of electrode or state of regeneration of electrode, water electrolysis methods or devices included to generate hydrogen to regenerate protons within the membrane as needed. The use of a gas diffusion electrode, which allows hydrogen gas passage through the flow analyzer and through the appropriate cell but retains water. Certain embodiments may include a series of flow analyzers having various charging membrane types. This arrangement is particularly useful to allow for a broader range of metal contaminant analysis. In certain embodiments, one metal may be removed at each stage of flow analysis, thereby not contaminating or interfering with subsequent stages of analysis. In certain embodiments, the order of operation and/or flow through a multistage cell may be important. In addition, material considerations in terms of the composition of the casing, enclosure, or other components may be important to contain fluid in the cell to inhibit loss of fluid during operation and analysis.

In certain embodiments, the use of gold (Au) nanofilm electrodes which have been physically vapor deposited (PVD) onto porous carbon paper substrates or other porous carbon media have been demonstrated to be capable of detecting concentrations below 10 μg/L of arsenite, As (III), in water. Nanofilms fabricated in such a manner may be characterized by scanning electron microscopy (SEM), X-ray diffraction and with X-ray fluorescence with a measured loading of approximately 13 μg of Au per 1 $cm^2$ of carbon paper in each electrode. This PVD method increases the manufacturability of aqueous arsenic sensors in a facile, scalable, and cost-effective manner, as it uses much less gold than alternate fabrication methods. Linear stripping voltammetry (LSV) has been used in a three-electrode configuration to create a calibration curve for standard additions of 5, 10, 25, 50 and 75 μg/L As (III). The resulting plot of peak area versus concentration resulted in a linear correlation. The capacitance of PVD deposited Au nano films has been measured to be significantly less than that of gold nanoparticles on XC72 carbon, produced via solution precipitation methods. The lower capacitance enables the detection of lower concentrations of arsenic without the need for the application of more complex pulse voltammetry methods.

In exemplary embodiments, an oxidation current may be selected that is proportional to the metal, selectivity of the flow analyzer cell by changing the potential within the cell. Potential is applied within the cell, the target analyte species is reduced to its metallic form, concentrated, and oxidized. Added advantages of the use of polymeric electrolytes in IEMs in flow analyzers as disclosed herein include the fact that if the electrical conditions are controlled, samples may be continuously analyzed. Flow analyzers according to exemplary embodiments, may be used to work in highly alkaline or acidic environments without leaking the acid or base into the stream due to the ion exchange, and due to the full flow analyzer enclosure. Certain embodiments may have one or more methods or processes automated to enable continuous monitoring of samples having various target analytes. Furthermore, miniaturization of such flow analyzers may be accomplished utilizing known microfluidic designs and methods known in the art.

Various applications of continuous analyte monitoring may be enabled using flow analyzers as disclosed herein. Ground water quality monitoring during seasonal changes in aquifers can be difficult in situations where water has the capacity to penetrate various geological features differently depending on seasonal changes. In such an instance, a continuous flow analyzer may provide a time-based series of continuous analysis of target analytes. The drilling of water wells may also benefit from such a continuous flow analyzer, as depth of drilling is usually selected by water quantity, however, this device may enable drawing water from wells having better quality as well as higher quantity of water. Other potential applications for such continuous flow analyzers include monitoring of mining contamination, remediation of industrial contamination. Certain municipalities or agencies may continuously monitor and therefore continuously remediate water quality entering water treatment facilities. With continuous monitoring, remediation can be applied in proportion to various contaminant concentration levels, and therefore lead to less costly treatments with lower environmental impact.

Figure 2:
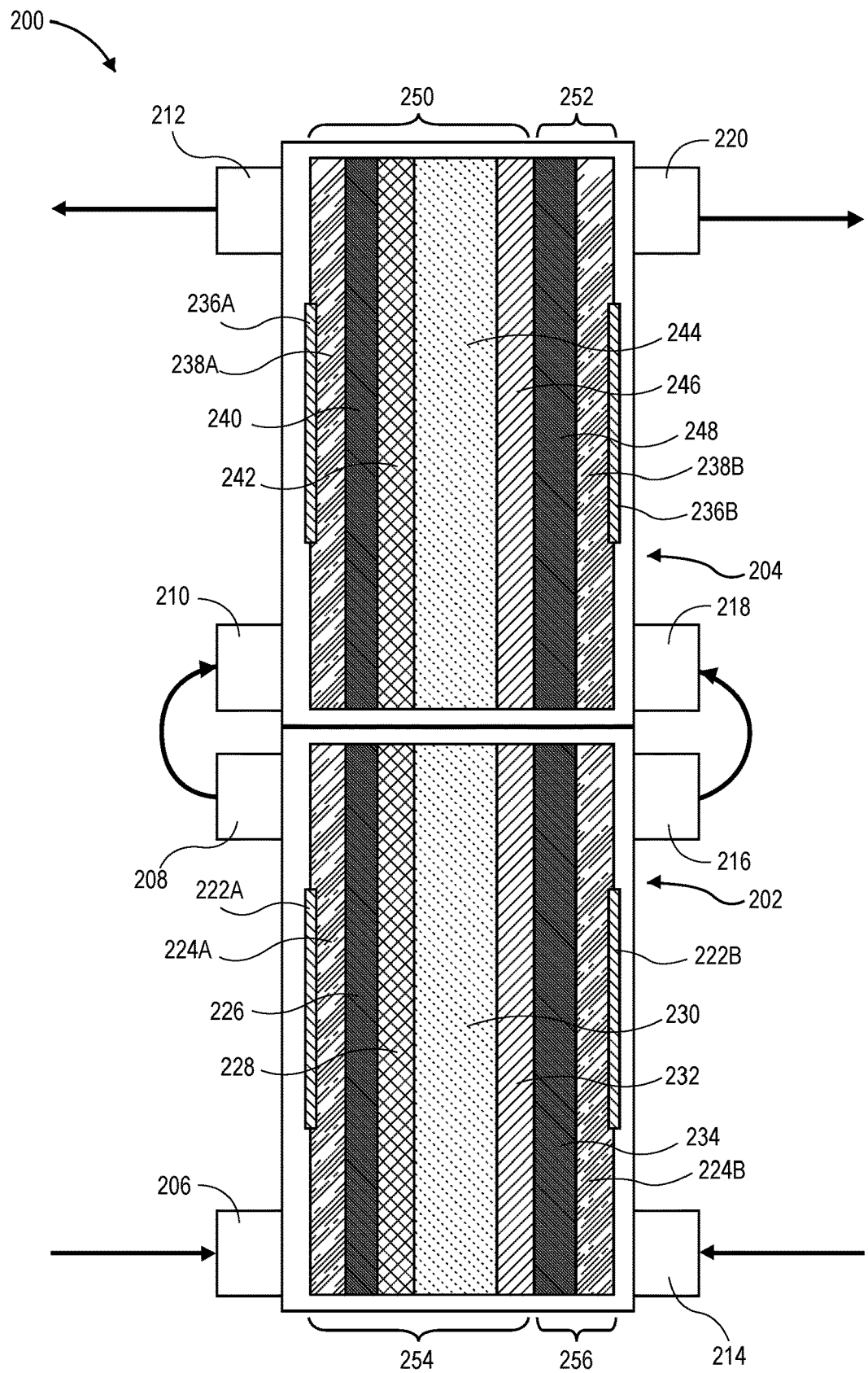
FIG. 2 is a cross-sectional schematic diagram of a flow analyzer having an array of electrochemical cells, according to an embodiment.

FIG. 2 is a cross-sectional schematic diagram of a flow analyzer having an array of electrochemical cells, according to an embodiment. FIG. 2 shows a flow analyzer having an array of two electrochemical cells, arranged to continuously analyze at least one target analyte in series. It should be noted that while the arrangement shown for the array of electrochemical cells illustrates two electrochemical cells arranged in series, alternate embodiments may be arranged such that there are more than two electrochemical cells, for example, three, four, or as many as ten electrochemical cells. Furthermore, certain embodiments of flow analyzers according to the general layout illustrated in FIG. 2 may be arranged in series, in parallel, or combinations thereof. The flow analyzer array 200 includes a first flow analyzer section 202 and a second flow analyzer section 204 which are shown adjacent to one another and enclosed within a single unit. It should be noted that certain embodiments may alternatively have separate enclosures for different flow analyzer sections or electrochemical cells, and need not be co-located with respect to one another, dependent upon the analyte(s) being measured, or the specific application in which the flow analyzer array 200 might be used. The first flow analyzer section 202 includes a first water inlet 206, wherein a water sample would be first introduced into the first flow analyzer section 202. As the first flooded zone 254 is filled with an aqueous sample for analysis, the sample could exit via a first water outlet 208 in the first flow analyzer section 202 and then into a second water inlet 210 on the second flow analyzer section 204. As the second flooded zone 250 is filled with the aqueous sample for analysis, the sample could exit the second flow analyzer section 204 via a second water outlet 212. While not shown here, a peristaltic pump or other fluid transport method known in the art may be used to pass an aqueous sample through the first flow analyzer section 202 and second flow analyzer section 204 of the flow analyzer array 200. In certain embodiments of a flow analyzer array 200, multiple sources of aqueous samples may be utilized to introduce aqueous sample to the flow analyzer array 200 for parallel operation as needed. On the opposite side of the flow analyzer array 200, in the first flow analyzer section 202, there is a first gas inlet 214 for the introduction of a gas into the first gas zone 256. As the first gas zone 256 of the first flow analyzer section 202 is filled, the gas then passes from the first gas zone 256, out through a first gas outlet 216 of the first flow analyzer section 202, and into a second gas inlet 218 of the second flow analyzer section 204 to fill the second gas zone 252 with gas. Once the second gas zone 252 is filled, the gas may then pass out through a second gas outlet 220 in the second flow analyzer section 204. It should be noted that although no means of gas transport is shown in this schematic, that various gas sources, gas regulators or other gas delivery devices known to those skilled in the art may be used in combination with the flow analyzer array 200. In certain embodiments of a flow analyzer array 200, multiple sources of gas sources may be utilized to introduce gas into the flow analyzer array 200 for parallel operation as needed.

The first flow analyzer section 202 of the flow analyzer array 200 further includes various layers similar in structure and function as those described in regard to the flow analyzer of FIG. 1. The first flow analyzer section 202 includes a first electrode lead material layer 224A on the working electrode side, a first electrode lead material layer 224B on the counter/reference electrode side, each having a lead material with an etched serpentine flow path. As before, the serpentine path is used to provide a maximized surface area for contact of the sample with the electrodes. The first flow analyzer section 202 also includes a first section working electrode metal 222A external to an internal plate of the first working electrode 224A for connecting the working electrode side of the cell to a potentiostat, and a first section counter/reference electrode metal 222B external to an internal plate of the first counter/reference electrode 224B for connecting the counter/reference side of the cell to a potentiostat. The first flow analyzer section 202 further includes, adjacent to the first electrode lead material layer 224A on the working electrode side, a first hydrophilic carbon felt conductive substrate for thin film 226, and a first thin film electrode 228, which in combination with the first electrode lead material layer 224A on the working electrode side, thin film 226, first thin film electrode 228, and metal plate 222A constitute the working electrode side in the first flow analyzer section 202. This first flooded flow through working electrode having a porous, hydrophilic media coated with a physically vapor deposited gold (Au) surface is encompassed by the first flooded zone 254 in the first flow analyzer section 202. The thin film electrode 228 may be composed of PVD gold or other materials as noted in regard to thin film electrode materials illustrated in FIG. 1. Adjacent to the thin film electrode 228 is an ion exchange membrane electrolyte 230, and adjacent to the ion exchange membrane electrolyte 230 is a first layer made of platinum (Pt) particles deposited onto a carbon substrate 232. The first ion exchange membrane 230 effectively separates the gas diffusion counter/reference electrode and the flooded flow through working electrode by ion selectivity, depending upon its composition. The Pt particles deposited on carbon 232, hydrophobic gas diffusion layer 234, electrode lead material 224B, and metal plate 222B constitute the counter/reference electrode side. This first gas diffusion counter/reference electrode is encompassed by the first gas zone 256 in the first flow analyzer section 202.

The second flow analyzer section 204 of the flow analyzer array 200 further includes various layers similar in structure and function as those described in regard to the flow analyzer of FIG. 1. The second flow analyzer section 204 includes a second electrode lead material layer 238A on the working electrode side, a second electrode lead material layer 238B on the counter/reference electrode side, each having a lead material with an etched serpentine flow path. As previously described, the serpentine path is used to provide a maximized surface area for contact of the sample with the electrodes. The second flow analyzer section 204 also includes a second section working electrode metal 236A external to an internal plate of the second working electrode 238A for connecting the working electrode side of the cell to a potentiostat, and a second section counter/reference electrode metal 236B external to an internal plate of the second counter/reference electrode 238B for connecting the counter/reference side of the cell to a potentiostat. The second flow analyzer section 204 further includes, adjacent to the second electrode lead material layer 238A on the working electrode side, a second hydrophilic carbon felt conductive substrate for thin film 240, and a second thin film electrode 242, which in combination with the second electrode lead material layer 238A on the working electrode side, thin film 240, second thin film electrode 242, and metal plate 236A constitute the working electrode side in the second flow analyzer section 204. This second flooded flow through working electrode having a porous, hydrophilic media coated with a physically vapor deposited gold (Au) surface is encompassed by the second flooded zone 250 in the second flow analyzer section 204. The thin film electrode 242 is composed of PVD gold, but may include other suitable materials. Adjacent to the thin film electrode 242 is an ion exchange membrane electrolyte 244, and adjacent to the ion exchange membrane electrolyte 244 is a second layer made of platinum (Pt) particles deposited onto a carbon substrate 246. The second ion exchange membrane 244 effectively separates the gas diffusion counter/reference electrode and the flooded flow through working electrode by ion selectivity, depending upon its composition. The Pt particles deposited on carbon 246, hydrophobic gas diffusion layer 248, electrode lead material 238B, and metal plate 236B constitute the counter/reference electrode side. This second gas diffusion counter/reference electrode is encompassed by the second gas zone 252 in the second flow analyzer section 204.

Each individual segment or component as listed in either the first flow analyzer section 202 or the second flow analyzer section 204 may have similar design elements or configurations, or operation parameters as described in regard to the flow analyzer of FIG. 1. For example, a first flow analyzer section 202 in a particular array may be operated in conjunction with the presence of or have included therein a first ion exchange membrane including an anionic ion exchange membrane while a second flow analyzer section 204 in a particular array may be operated in conjunction with the presence of or have included therein a first ion exchange membrane including cationic ion exchange membrane, although any of the aforementioned arrangements with respect to ion exchange membrane and its particular operating principles may be utilized in any or several of the flow analyzer sections in a particular array in exemplary embodiments. A flow analyzer array 200 as shown and described in regard to FIG. 2 may further have a single stack fuel cell casing that encases the first electrochemical cell and the second electrochemical cell, or in alternative embodiments, may have a first and second electrochemical cell housed in different casings or enclosures. It should be noted that if different electrochemical cells are enclosed or housed in separate or different enclosures, they would be connected by the appropriate pumps, gas sources or other plumbing required to transport either aqueous samples or gas sources to the appropriate zones of each cell.

Figure 3:
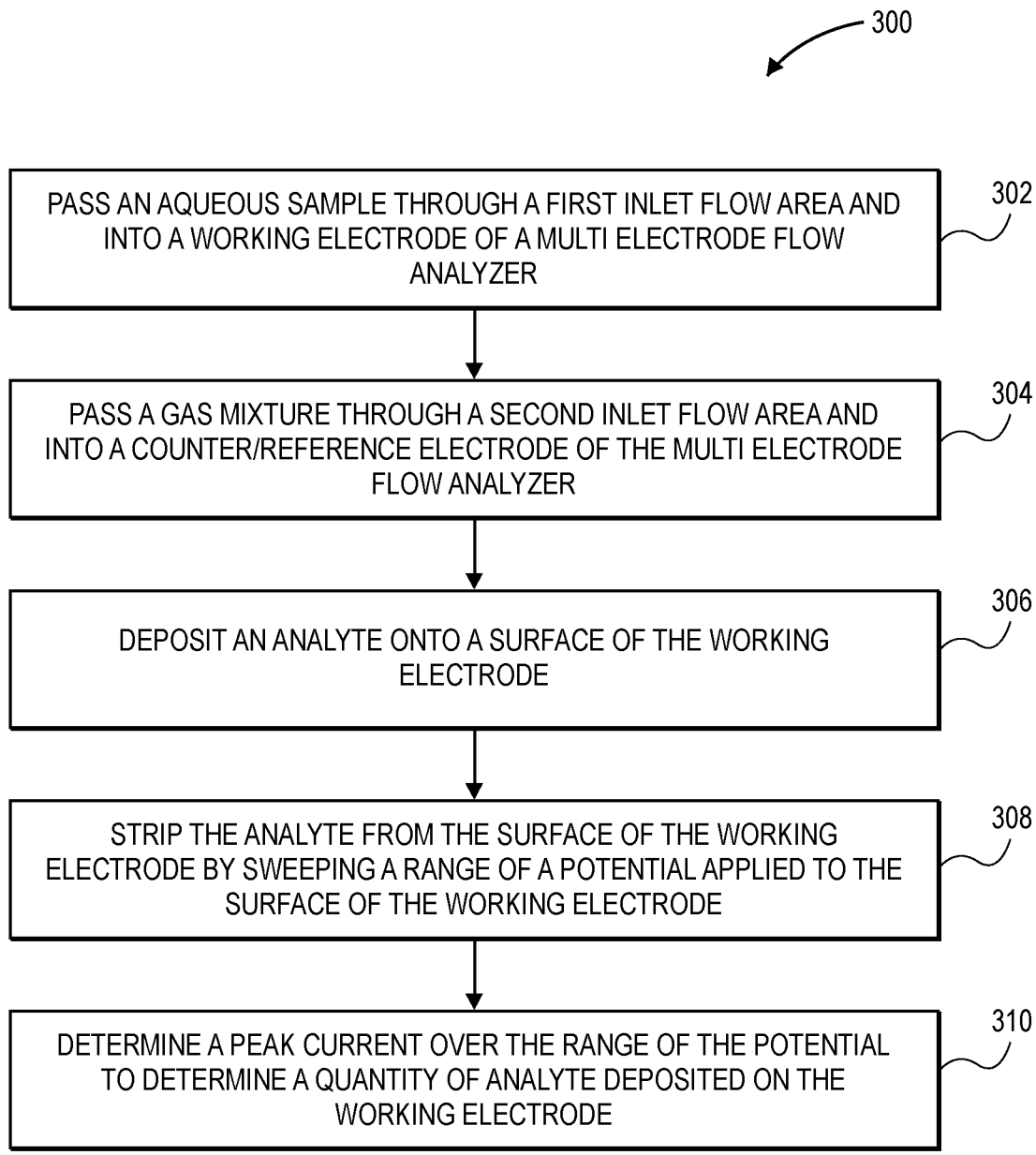
FIG. 3 is a flowchart illustrating a method of continuous fluid analysis using a multi-electrode flow analyzer, according to an embodiment.

FIG. 3 is a flowchart illustrating a method of continuous fluid analysis using a multi-electrode flow analyzer, according to an embodiment. The method of continuous fluid analysis using a multi-electrode flow analyzer 300 includes passing an aqueous sample through a first inlet flow area and into a working electrode of a multi-electrode flow analyzer 302, followed by passing a gas mixture through a second inlet flow area and into a counter/reference electrode of the multi-electrode flow analyzer 304. The method of continuous fluid analysis using a multi-electrode flow analyzer 300 then includes depositing an analyte onto a surface of the working electrode 306, stripping the analyte from the surface of the working electrode by sweeping a range of a potential applied to the surface of the working electrode 308, and finally, determining a peak current over the range of the potential to determine a quantity of analyte deposited on the working electrode 310. Certain embodiments of the method of continuous fluid analysis using a multi-electrode flow analyzer may also include reducing any aqueous metal ions present on the surface of the working electrode prior to stripping the analyte from the surface of the working electrode. In some embodiments, the method of continuous fluid analysis using a multi-electrode flow analyzer may include oxidizing any aqueous metal ions present on the surface of the working electrode prior to stripping the analyte from the surface of the working electrode. The method of continuous fluid analysis using a multi-electrode flow analyzer may incorporate a step of depositing an analyte onto a surface of the working electrode which includes holding the working electrode at a negative potential. The method of continuous fluid analysis using a multi-electrode flow analyzer may incorporate a step of sweeping a range of a potential on the surface of the working electrode is from a positive value to a negative value. The foregoing method steps may, in certain embodiments, may include the use of a continuous flow analyzer having a single electrochemical cell, or a continuous flow analyzer having multiple electrochemical cells. In these embodiments, the electrochemical cells in a continuous flow analyzer having multiple electrochemical cells may work on similar or different operating principles as described herein.

Figure 4:
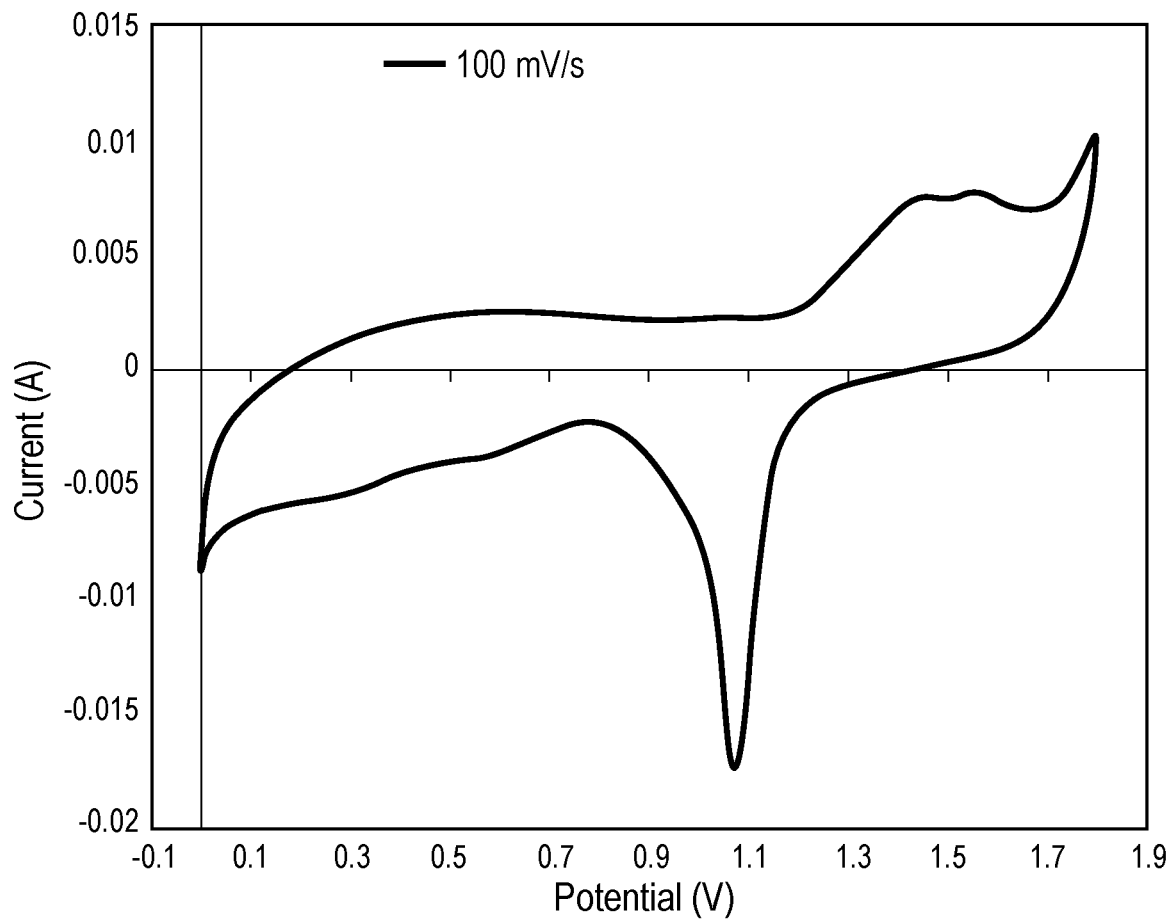
FIG. 4 is a data plot demonstrating cyclic voltammetry of a flow analyzer having a gold electrode taken in a flowing stream of water, according to an embodiment.

FIG. 4 is a data plot demonstrating cyclic voltammetry of a flow analyzer having a gold electrode taken in a flowing stream of water, according to an embodiment. FIG. 4 illustrates experimental results exhibiting the cyclic voltammetry of a gold electrode taken in a flowing stream of water having a quantity of aqueous arsenite, As (III). The data was collected at 100 mV/s. This data demonstrates that electrochemistry can be performed in a flow-through analyzer as described herein, and without the injection of an acid electrolyte. This type of analysis is commonly done before stripping voltammetry is performed to show that the working electrode is active. These experimental results were conducted by using a platinum counter electrode and flowing 4% $H_2$ gas over the counter electrode, thus creating a counter/reference electrode and eliminating one electrode. Furthermore, by using an ion exchange membrane in a flow-though analysis configuration the samples could be measured at their natural pH without prior sample modification. The cyclic voltammetry results exhibit a fairly typical shape as expected from cyclic voltammetry results when measuring similar analytes.

While the present teachings have been illustrated with respect to one or more implementations, alterations and/or modifications may be made to the illustrated examples without departing from the spirit and scope of the appended claims. For example, it may be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings. It may be appreciated that structural objects and/or processing stages may be added, or existing structural objects and/or processing stages may be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items may be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the illustrated embodiment. The terms "couple," "coupled," "connect." "connection," "connected," "in connection with," and "connecting" refer to "in direct connection with" or "in connection with via one or more intermediate elements or members." Finally, the terms "exemplary" or "illustrative" indicate the description is used as an example, rather than implying that it is an ideal. Other embodiments of the present teachings may be apparent to those skilled in the art

What is claimed is:

1. An electrochemical cell for detecting heavy metals in water, comprising:
   a gas diffusion counter/reference electrode;
   a gas inlet in communication with the gas diffusion counter/reference electrode, wherein the gas inlet is connected to a hydrogen source that is external to the electrochemical cell;
   a flooded flow through working electrode;
   a water inlet in communication with the flooded flow through working electrode, wherein the water inlet is configured to be connected to a water source that is external to the electrochemical cell; and
   an ion exchange membrane comprising a composition selected based on a heavy metal being detected and disposed to separate the gas diffusion counter/reference electrode and the flooded flow through working electrode; and
   a flooded zone; and wherein:
   the working electrode comprises a physically vapor deposited gold (Au) film, the working electrode configured to receive deposition of a heavy metal on a surface of the working electrode, and configured to remove the heavy metal from the surface of the working electrode; and
   the flooded flow through working electrode is positioned in the flooded zone and separated from the gas diffusion counter/reference electrode by the ion exchange membrane, wherein the ion exchange membrane directly contacts both the flooded flow through working electrode and the gas diffusion counter/reference electrode.

2. The electrochemical cell of claim 1, wherein the counter/reference electrode comprises a platinum (Pt) electrode.

3. The electrochemical cell of claim 1, wherein the working electrode further comprises a hydrophilic surface.

4. The electrochemical cell of claim 1, wherein the working electrode further comprises a porous carbon media.

5. The electrochemical cell of claim 1, wherein the working electrode further comprises an internal serpentine fluidic pathway.

6. The electrochemical cell of claim 1, wherein the ion exchange membrane comprises a cationic exchange membrane.

7. The electrochemical cell of claim 1, wherein the ion exchange membrane comprises an anionic exchange membrane.

8. The electrochemical cell of claim 1, wherein the ion exchange membrane comprises an exchange membrane designed for use in a pH range of from about 6 to about 9.

9. The electrochemical cell of claim 1 further comprising a single stack fuel cell casing that encases the counter/reference electrode, the working electrode, and the ion exchange membrane.

10. The electrochemical cell of claim 1 further comprising at least one inlet on a first side of the electrochemical cell, and at least one outlet on a second side of the electrochemical cell.

11. The electrochemical cell of claim 1 further comprising a first inlet and a first outlet on a first side of the electrochemical cell, and a second inlet and a second outlet on a second side of the electrochemical cell.

12. An array of two or more electrochemical cells for detecting heavy metals in water, comprising:
   a first electrochemical cell comprising:
      a first gas diffusion counter/reference electrode;
      a first flooded flow through working electrode comprising a porous, hydrophilic media coated with a physically vapor deposited gold (Au) surface;
      a first flooded zone; and
      a first ion exchange membrane comprising a first ion exchange membrane composition selected based on a heavy metal being detected and disposed to separate the first gas diffusion counter/reference electrode and the first flooded flow through working electrode;
   a second electrochemical cell comprising:
      a second gas diffusion counter/reference electrode;
      a second flooded flow through working electrode comprising a porous, hydrophilic media coated with a bismuth surface; and
      a second ion exchange membrane comprising a second ion exchange membrane composition selected based on a heavy metal being detected that is disposed to separate the second gas diffusion counter/reference electrode and the second flooded flow through working electrode to form an anoxic environment around the gas diffusion counter/reference electrode;
   a gas inlet in communication with the first gas diffusion counter/reference electrode and the second gas diffusion counter/reference electrode connected to a hydrogen source that is external to the electrochemical cell;
   a water inlet in communication with the first flooded flow through working electrode and the second flooded flow through working electrode and configured to be connected to a water source that is external to the electrochemical cell;
   a second flooded zone; and wherein:
   each working electrode is configured to receive deposition of a heavy metal on a surface of the working electrode, and configured to remove the heavy metal from the surface of the working electrode;
   the first flooded flow through working electrode is positioned in the first flooded zone and separated from the first gas diffusion counter/reference electrode by the first ion exchange membrane, wherein the first ion exchange membrane directly contacts both the first flooded flow through working electrode and the first gas diffusion counter/reference electrode; and
   the second flooded flow through working electrode is positioned in the second flooded zone and separated from the second gas diffusion counter/reference electrode by the second ion exchange membrane, wherein the first ion exchange membrane directly contacts both the first flooded flow through working electrode and the first gas diffusion counter/reference electrode.

13. The array of two or more electrochemical cells of claim 12, further comprising a single stack fuel cell casing that encases the first electrochemical cell and the second electrochemical cell.

14. The array of two or more electrochemical cells of claim 12, wherein the first ion exchange membrane further comprises an anionic exchange membrane.

15. The array of two or more electrochemical cells of claim 12, wherein the second ion exchange membrane further comprises a cationic exchange membrane.

16. The array of two or more electrochemical cells of claim 12, wherein the first electrochemical cell and the second electrochemical cell are configured in series.

17. A method of continuous fluid analysis for heavy metals in water using a multi-electrode flow analyzer, comprising:
passing an aqueous sample through a first water inlet flow area and into a flooded flow working electrode of a multi-electrode flow analyzer;
passing a gas mixture through a second gas inlet flow area and into a gas diffusion counter/reference electrode of the multi-electrode flow analyzer;
depositing an analyte onto a surface of the working electrode, which comprises a physically vapor deposited gold (Au) film;
stripping the analyte from the surface of the working electrode by sweeping a range of a potential applied to the surface of the working electrode; and
determining a peak current over the range of the potential to determine a quantity of analyte deposited on the working electrode; and wherein:
the flooded flow through working electrode is positioned in a flooded zone and separated from the gas diffusion counter/reference electrode by an ion exchange membrane, the ion exchange membrane comprising a composition selected based on a heavy metal being detected and disposed to directly contact both the flooded flow through working electrode and the gas diffusion counter/reference electrode and separate the gas diffusion counter/reference electrode from the flooded flow through working electrode;
the water inlet is configured to be connected to a water source that is external to the multi-electrode flow analyzer; and
wherein the gas inlet is connected to a hydrogen source that is external to the multi-electrode flow analyzer.

18. The method of continuous fluid analysis using a multi-electrode flow analyzer of claim 17, further comprising reducing any aqueous metal ions present on the surface of the working electrode prior to stripping the analyte from the surface of the working electrode.

19. The method of continuous fluid analysis using a multi-electrode flow analyzer of claim 17, further comprising oxidizing any aqueous metal ions present on the surface of the working electrode prior to stripping the analyte from the surface of the working electrode.

20. The method of continuous fluid analysis using a multi-electrode flow analyzer of claim 17, wherein depositing an analyte onto a surface of the working electrode further comprises holding the working electrode at a negative potential.

21. The method of continuous fluid analysis using a multi-electrode flow analyzer of claim 17, wherein sweeping a range of a potential on the surface of the working electrode is from a positive value to a negative value.

* * * * *